(12) United States Patent
Battles et al.

(10) Patent No.: US 6,860,882 B2
(45) Date of Patent: Mar. 1, 2005

(54) ELECTRO-SURGICAL BIPOLAR FORCEPS

(75) Inventors: Christopher Austin Battles, New Haven, CT (US); Paul DiCesare, Easton, CT (US); Patrick Gutelius, Shelton, CT (US); Daniel Paul Ferriera, Milford, CT (US); Richard Barry Stevens, Mashpee, MA (US); John Buonanno, Bristol, RI (US); Donald A. Coelho, Jr., Bellingham, MA (US); Sharon A. Mulligan, Attleboro, MA (US)

(73) Assignee: Codman & Shurtleff, Inc., Raynham, MA (US)

( * ) Notice: Subject to any disclaimer, the term of this patent is extended or adjusted under 35 U.S.C. 154(b) by 0 days.

(21) Appl. No.: 10/457,176

(22) Filed: Jun. 9, 2003

(65) Prior Publication Data

US 2004/0158242 A1 Aug. 12, 2004

Related U.S. Application Data

(63) Continuation-in-part of application No. 10/359,495, filed on Feb. 6, 2003.

(51) Int. Cl.[7] ............................................... A61B 18/18
(52) U.S. Cl. .......................................... 606/51; 606/52
(58) Field of Search .............................. 606/41, 48–52, 606/205–207

(56) References Cited

U.S. PATENT DOCUMENTS

| 4,041,952 | A | * | 8/1977 | Morrison et al. ............. 606/42 |
|---|---|---|---|---|
| 5,647,871 | A | * | 7/1997 | Levine et al. ................. 606/45 |
| 5,902,301 | A | | 5/1999 | Olig |
| 6,110,171 | A | * | 8/2000 | Rydell .......................... 606/51 |
| 6,210,411 | B1 | * | 4/2001 | Hofmann et al. ............. 606/52 |
| 6,800,077 | B1 | * | 10/2004 | Mucko et al. ................ 606/51 |
| 2002/0016591 | A1 | * | 2/2002 | Levine et al. ................. 606/51 |

FOREIGN PATENT DOCUMENTS

| FR | 1 536 272 A | 8/1968 |
|---|---|---|
| FR | 95 614 E | 2/1971 |
| FR | 2 562 788 A | 10/1985 |

OTHER PUBLICATIONS

Narakas A, et al.; Electrically Actuated Grip For Surgery; Oct. 18, 1985, Derwent World Patents Index, 2004 Derwent Information Ltd.; Dialog File No. 351 Accession No. 4471305; Abstract.

European Search Report EP 04250665 dated May 19, 2004.

* cited by examiner

Primary Examiner—Michael Peffley

(57) ABSTRACT

In accordance with a currently preferred exemplary embodiment, the present invention involves an electro-surgical bipolar forceps having a first member, a second member, and a tip assembly. The first member has a first insert tube extending from a distal end thereof and a handle disposed at a proximal end thereof. The second member has a second insert tube extending from a distal end thereof and a handle disposed at a proximal end thereof. At least one of the first and second insert tube has an inner surface, a portion of which is covered with an electrically insulating material. The first tip assembly has a proximal end and a distal end. The proximal end of the first tip assembly is selectively engageable with one of the first and second insert tubes. The first tip assembly includes an electrically conductive tip disposed at the distal end of the first tip assembly.

9 Claims, 10 Drawing Sheets

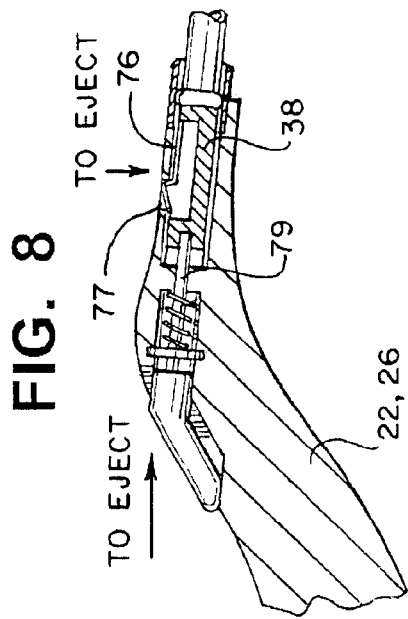
FIG. 7
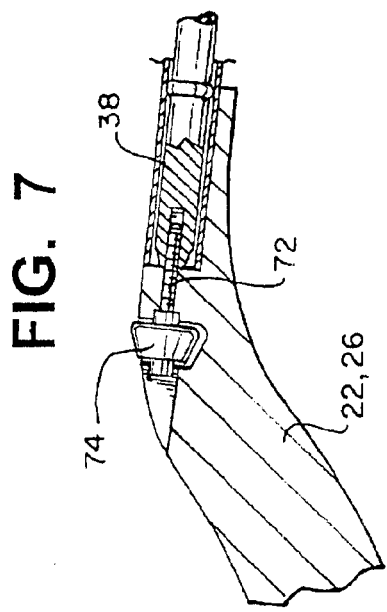
FIG. 8
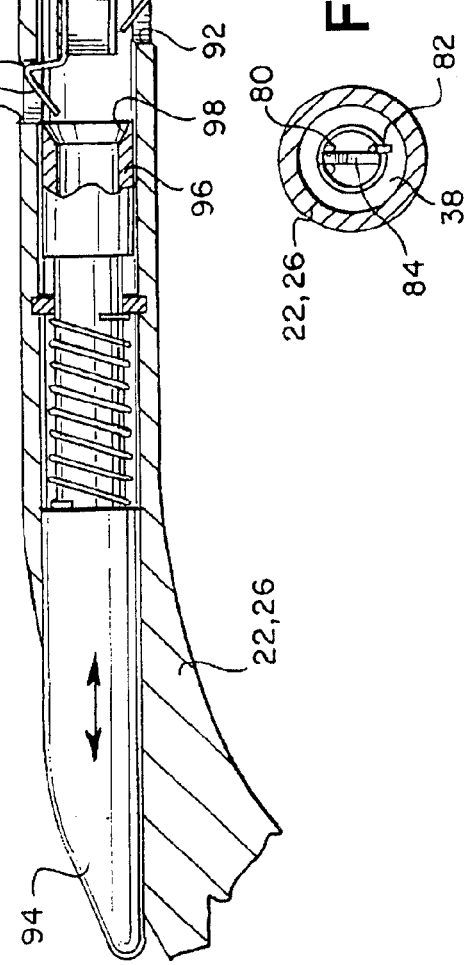
FIG. 9A
FIG. 9C

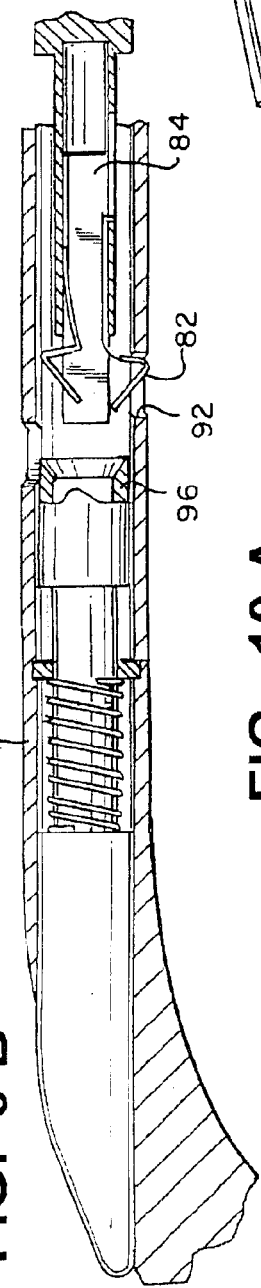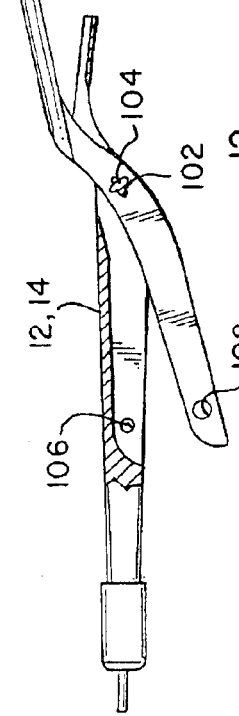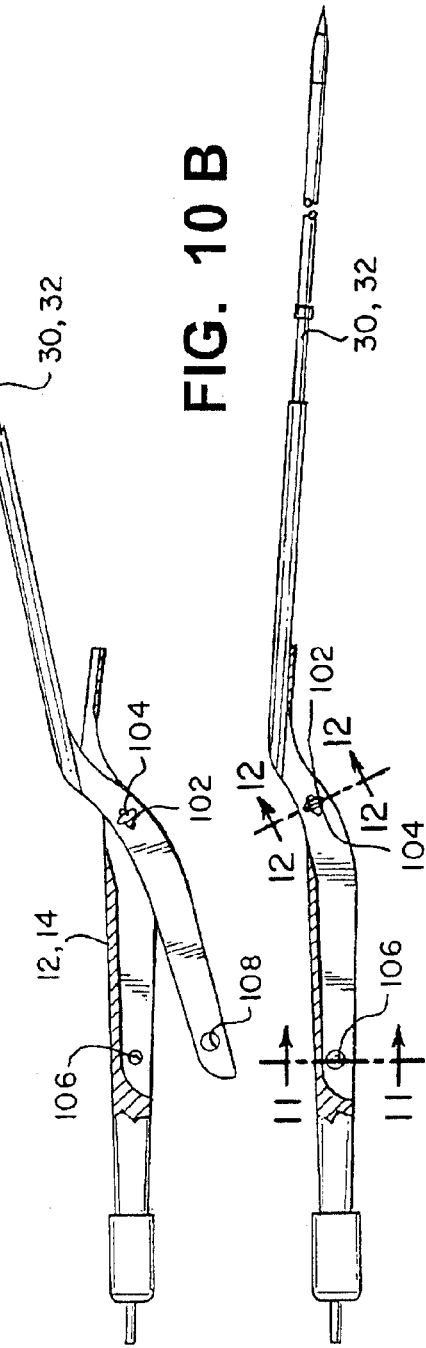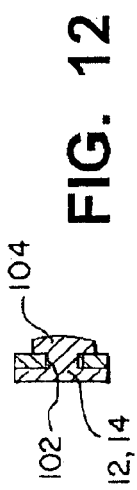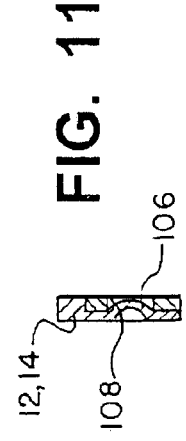

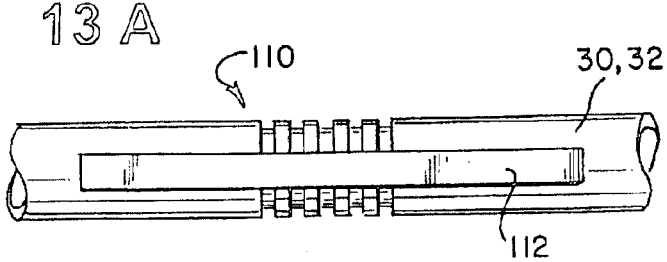
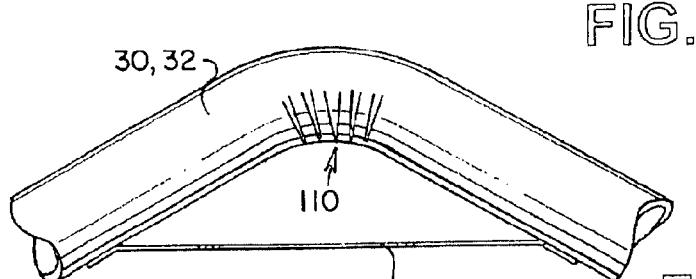
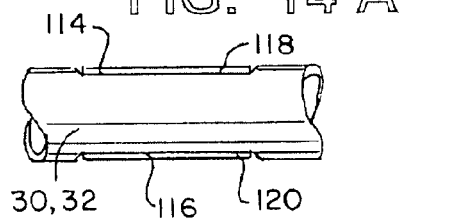 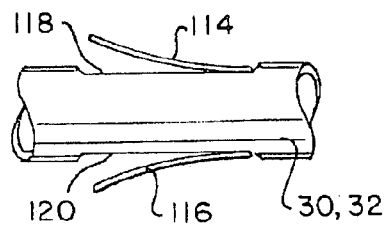
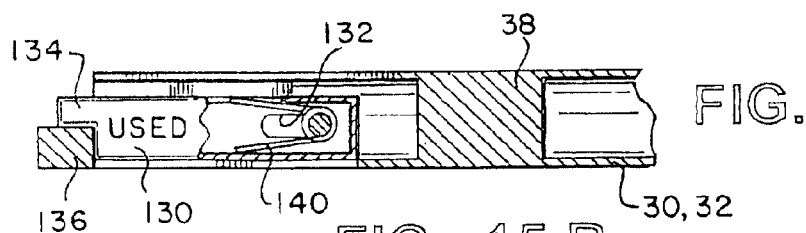
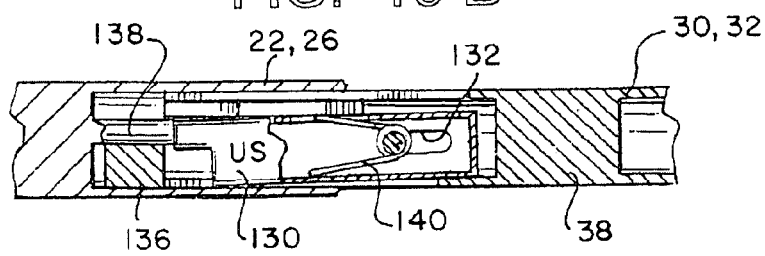

ELECTRO-SURGICAL BIPOLAR FORCEPS

This application is a Continuation-In-Part of currently pending application Ser. No. 10/359,495, filed Feb. 6, 2003, entitled Electro-Surgical Bipolar Forceps, the disclosure of which is hereby incorporated by reference in its entirety.

BACKGROUND OF THE INVENTION

1. Field of the Invention

The present invention relates to a electro-surgical bipolar forceps, and more particularly, to electro-surgical bipolar forceps that have replaceable tip assemblies.

2. Discussion of Related Art

Electro-surgical bipolar forceps are known in the art, and are commonly used in surgical procedures to grasp, dissect, seal and clamp tissue. Bipolar forceps comprise a pair of tips, and each tip comprises an electrode in communication with a source of electrical power. In most cases, the tips are fixedly attached to the handles. Therefore, to reuse these types of bipolar forceps, the bipolar forceps must be sterilized between each use. In addition, after multiple uses the tips of the forceps often become misaligned thereby requiring returning the forceps to the manufacturer for realignment, if possible.

U.S. Pat. No. 6,050,996 to Schmaltz et al. discloses a bipolar electro-surgical instrument that has replaceable electrodes. But these replaceable electrodes do not permit the tip assembly to vary in shape and size. In addition, these replaceable electrodes do not address the problem of correcting misaligned jaws. Accordingly, there is still a need in the art for electro-surgical bipolar forceps that have replaceable tip assemblies. Thus, the tips would no longer be subject to a sterilization process as they can simply be disposed of and replaced with a new pair of tips. In addition, the new tip assembly would automatically align in the proper orientation. Further, the use of multiple tip assemblies permit the length and shape of the tips to vary depending upon the needs of the surgeon.

SUMMARY OF THE INVENTION

In accordance with a currently preferred exemplary embodiment, the present invention includes an electro-surgical bipolar forceps having a first member, a second member, and a tip assembly. The first member has a first insert tube extending from a distal end thereof and a handle disposed at a proximal end thereof. The second member has a second insert tube extending from a distal end thereof and a handle disposed at a proximal end thereof. At least one of the first and second insert tube has an inner surface, a portion of which is covered with an electrically insulating material. The first tip assembly has a proximal end and a distal end. The proximal end of the first tip assembly is selectively engageable with one of the first and second insert tubes. The first tip assembly includes an electrically conductive tip disposed at the distal end of the first tip assembly.

In accordance with another currently preferred exemplary embodiment, the present invention includes a first distal seal disposed about a first oversheath sleeve and adjacent to a proximal end of a first spacer sleeve. The first distal seal is comprised of an inner seal and an outer seal. The outer seal having a longitudinal length that is greater than a length of the inner seal. The outer seal has a portion spaced radially outwardly from the first oversheath sleeve by approximately the same predetermined dimension as the radial thickness of the distal end of the first insert tube.

BRIEF DESCRIPTION OF THE DRAWINGS

The above and still further objects, features and advantages of the present invention will become apparent upon consideration of the following detailed description of a specific embodiment thereof, especially when taken in conjunction with the accompanying drawings wherein like reference numerals in the various figures are utilized to designate like components, and wherein:

FIG. 7 is a partial cross-sectional view showing the tip assembly being selectively engaged with the insert tube by a threaded connection that includes a rotatable knob;

FIG. 8 is a cross-sectional view showing the tip assembly being selectively engageable with the insert tube by a spring;

FIG. 9A is a partial cross-sectional view showing the tip assembly being selectively engageable with the insert tube by a leaf spring;

FIG. 9B is a partial cross-sectional view showing the tip assembly of FIG. 9A being disengaged from the insert tube;

FIG. 9C is a cross-sectional view taken along line 9C—9C of FIG. 9A and looking in the direction of the arrows.

FIG. 10A is a side view, with parts in partial cross-section, showing an electro-surgical bipolar forceps having the tip assembly selectively engaged with the insert tube by a bayonette connection;

FIG. 10B is a side view of the bipolar forceps of FIG. 10 shown in the selectively engaged position;

FIG. 11 is a cross-sectional view taken along the line 11—11 of FIG. 10B and looking in the direction of the arrows;

FIG. 12 is a cross-sectional view taken along the lines 12—12 of FIG. 10B and looking in the direction of the arrows;

FIG. 13A is a partial side view of the tip assembly in accordance with another embodiment of the present invention;

FIG. 13B is a partial side view of the tip assembly of FIG. 13A, and shown in a bent configuration;

FIG. 14A is a partial side view of the tip assembly in accordance with another embodiment of the present invention;

FIG. 14B is a partial side view of the tip assembly of FIG. 14A, shown after being subject to a thermal load;

DETAILED DESCRIPTION OF THE CURRENTLY PREFERRED EXEMPLARY EMBODIMENT

Figure 1:
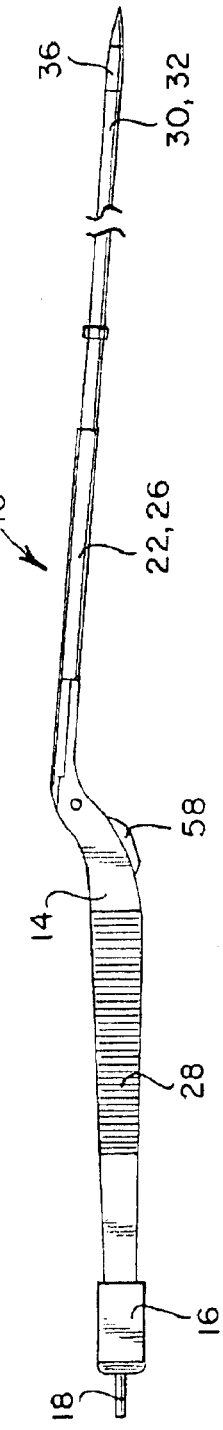
FIG. 1 is a side view of the electro-surgical bipolar forceps in accordance with the present invention.
Figure 2:
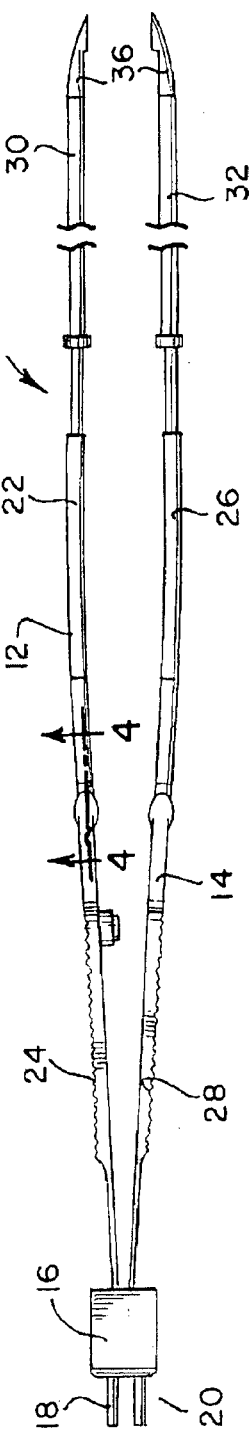
FIG. 2 is a top view of the electro-surgical bipolar forceps of FIG. 1.

Referring now to FIGS. 1 though 5, an electro-surgical bipolar forceps 10, in accordance with the present invention, is illustrated. Forceps 10 include a first member 12 and a second member 14, which are connected together by a connector 16. Each member 12, 14 is electrically insulated from the other member within connector housing 16 and is connected to a corresponding contact pin 18, 20. Contact pins 18, 20 are configured to be connected to a power source, in a manner known to those skilled in the art. First member 12 has a first insert tube 22 disposed at a distal end thereof and a handle 24 disposed at a proximal end thereof. Likewise, second member 14 has a second insert tube 26 disposed at a distal end thereof and a handle 28 disposed at a proximal end thereof.

Insert tubes 22, 26 are illustrated as being cylindrical in shape, but are not to be limited to this shape. Of course, insert tubes 22, 26 can be of other closed or even open shapes, such as, for example, square, rectangular, and other polygonal or other irregular shapes.

Figure 3A:
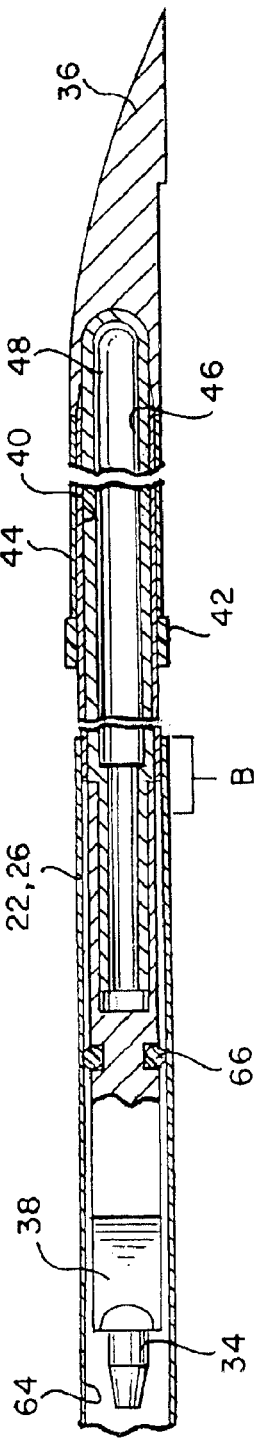
FIG. 3A is a partial cross-sectional view of the tip assembly and insert tube of the electro-surgical bipolar forceps of FIG. 1.

Forceps 10 also include a first tip assembly 30 that is selectively engageable with either first insert tube 22 or second insert tube 26 (in the illustration, first tip assembly 30 is shown selectively engaged with the first insert tube 22). A second tip assembly 32 is selectively engageable either with first insert tube 22 or second insert tube 26. Each tip assembly 30, 32 has a proximal end 34 and a distal end 36, as illustrated in FIG. 3A. The proximal end of the tip assembly is preferably selectively engageable with either insert tube 22, 26. Each tip assembly 30, 32 includes an engagement plug 38, an oversheath sleeve 40, an electrically conductive tip 36, and a distal seal 42. In addition, each tip assembly may include a spacer sleeve 44 so that the length of the tip assembly can vary. Further, the shapes of the tips can vary depending upon the needs of the surgeon. Additionally, a heat pipe 46 is preferably disposed within the oversheath sleeve 40 and between the engagement plug 38 and tip 36. Heat pipe 46 is totally enclosed in sealed chamber 48 and is effective to remove heat from the tip 36. The use of a heat pipe in bipolar forceps is known from the teaching of U.S. Pat. Nos. 6,074,389 and 6,206,876, and pending U.S. Application Pub. No. 2002/0016591A1, the disclosures of these patents and patent application are each hereby incorporated by reference in their entirety.

Figure 3B:
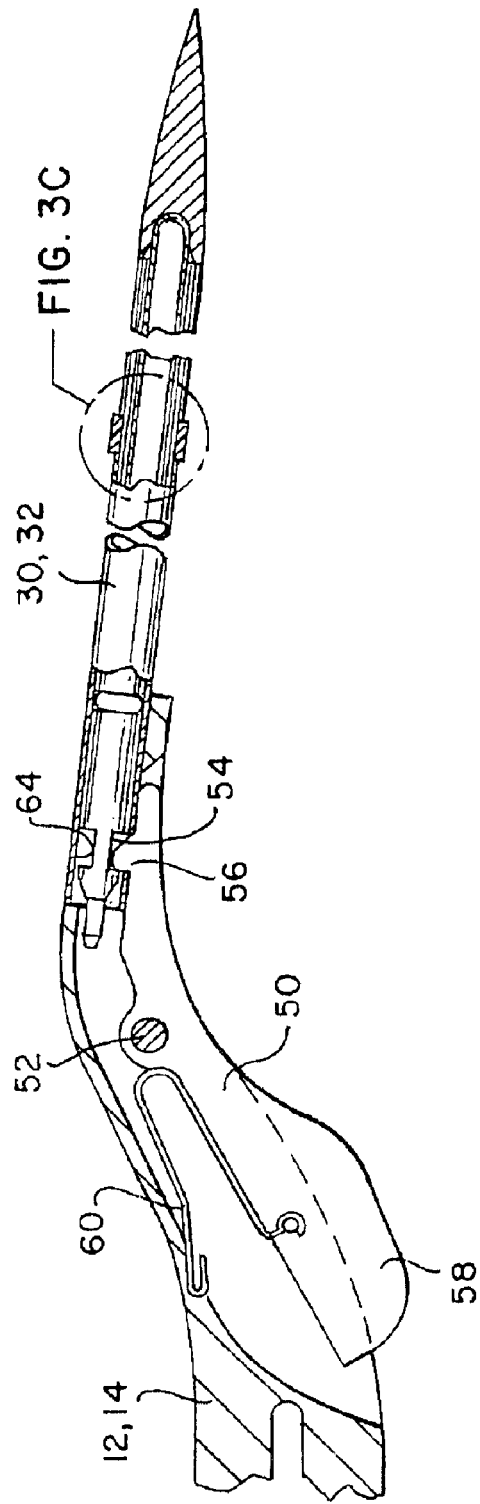
FIG. 3B is a partial cross-sectional view of the tip assembly shown in the selectively-engaged position with respect to the insert tube.
Figure 4:
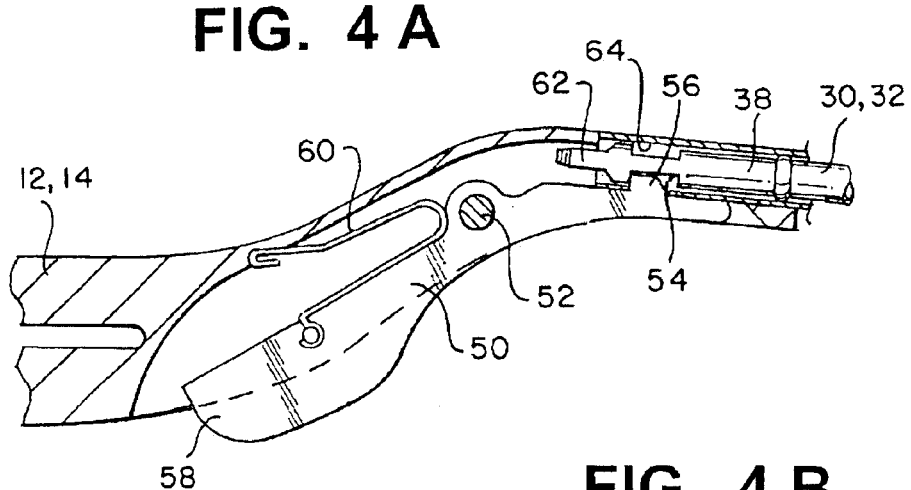
FIG. 4A is a partial cross-sectional view showing the tip assembly in the selectively-engaged position with respect to the insert tube.
FIG. 4B is a partial cross-sectional view showing the tip assembly being selectively disengaged with respect to the insert tube.
Figure 4:
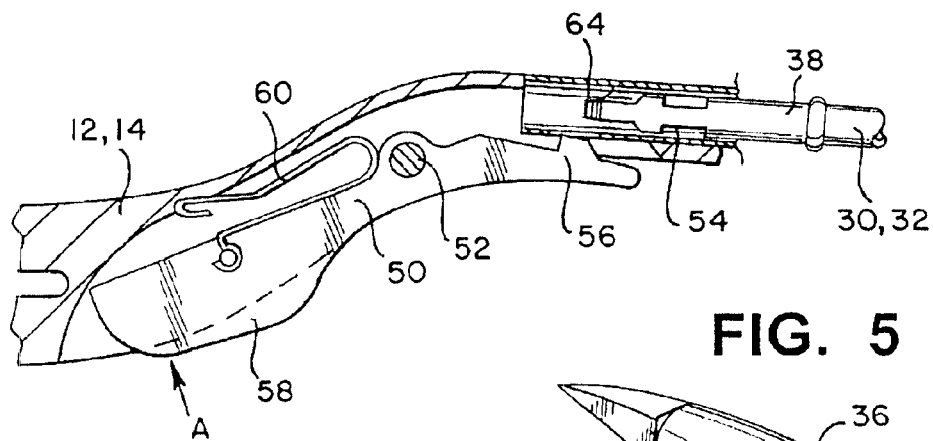
Figure 5:
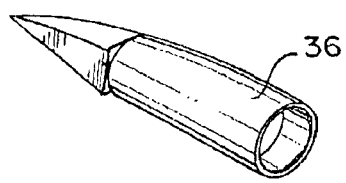
FIG. 5 is a perspective view of the tip of the tip assembly.

Each member 12, 14 includes a release button 50 that is connected to insert tube 22, 26 by a pivot pin connection 52. As illustrated in FIGS. 3B, 4A and 4B, engagement plug 38 has a recess 54. Recess 54 is shaped to receive a locking shoulder 56 disposed at one end of the release button 50. Release button 50 has a release tab 58 disposed at an opposite end from locking shoulder 56. A spring 60 is connected to member 12, 14 at one end and to release button 50 at an opposite end. Spring 60 normally biases releases button 50 into the locked position shown in FIG. 4A. The release button is moveable from the locked position to the unlocked position by the application of an external force in the direction indicated by arrow A in FIG. 4B. For example, a surgeon may depress release tab 58 in the direction indicated by arrow A to thereby move locking shoulder 56 away from recess 54 in the engagement plug 38. Once release tab 58 is sufficiently depressed, the surgeon may thereafter grasp the tip assembly and remove the entire tip assembly 30, 32 from the respective insert tube 22, 26. During insertion of a tip assembly 30, 32 into the respective insert tube 22, 26, the operator can manually insert the tip assembly 30, 32 such that the proximal end, or engagement plug 38, is received within the insert tube 22, 26. The extreme end 62 of engagement plug 38 may have a keyed shape, such as a square, to be matingly received within a correspondingly-shaped socket within the insert tube to ensure that the tip assembly is aligned in the proper orientation with respect to the other tip assembly. As shown in FIG. 1, release tab 58 is disposed on a "lower" end of the forceps 10. Thus, during use, a surgeon can look down the "upper" portion of the forceps with an unobstructed view of the surgical site.

Each insert tube 12, 14 has an inner surface 64. Inner surface 64 is preferably covered or coated with an electrically-insulating material. Thereafter, a portion of that coating or covering is removed at the distal end of the inner surface of the insert tube so that this portion of the inner surface of the insert tube is electrically conductive. The electrically conductive inner surface portion of the insert tube, in a selectively-engaged position of the tip assembly within the insert tube, is located distally with respect to a proximal seal 66. For example, as illustrated in FIG. 3A, only predetermined portion B of the inner surface of the insert tube has the insulating material removed therefrom.

Figure 3C:
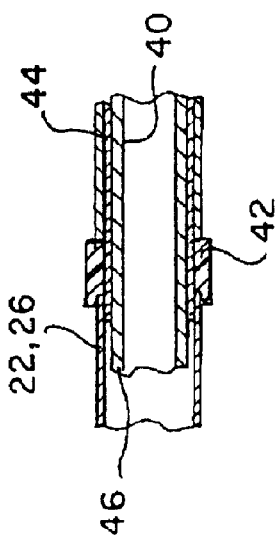
FIG. 3C is an enlarged cross-sectional detail taken from the detailed circle of FIG. 3B.

Proximal seal 66 is disposed about the proximal end of the tip assembly 30, 32. In the selectively-engaged position, proximal seal 66 is disposed between the proximal end of the tip assembly 30, 32 and the insert tube 22, 26, as illustrated in FIGS. 3A, 3B and 4A. Oversheath sleeve 40 is disposed between the engagement plug 38 and the tip 36. Spacer sleeve 44 is disposed adjacent to the tip 36 and about the oversheath sleeve 40. Distal seal 42 is disposed about the oversheath sleeve 40 and adjacent to proximal end of spacer sleeve 44, as shown in FIG. 3A. In the selectively-engaged position, distal seal 42 is disposed in contact with spacer sleeve 44 and one of the insert tubes 22, 26, or alternatively, should no spacer sleeve 44 be used, then in contact with tip 36 and one of the insert tubes 22, 26. As illustrated in FIG. 3C, in the selectively-engaged position, distal seal 42 is compressed between the spacer sleeve 44, and the insert tube 22, 26. Thus, a force is applied in the distal direction on the spacer sleeve. As pointed out above, spacer sleeve may be of various lengths to vary the length of the tip assembly. Alternatively, no spacer sleeve may be used to shorten the tip assembly to its shortest dimension. In this situation, the distal seal 42 would be compressed between the tip 36 and the insert tube 22, 26.

The current path from contact pins 18, 20 to the tips 36 extends from pin 18, 20, through the handle 24, 28 (of course, the outer portion of the handle, insert tube and most of the tip assembly can be covered with an insulating material to electrically isolate the member and tip assemblies from each other and from the user), to the insert tube 22, 26, to the oversheath sleeve 40 where they contact the insert tube in area B, to the heat pipe 46 to the tip 36. Tips 36 are preferably made of copper and coated with gold or other biocompatible material. In use, fluid may collect in and around button 50 and on the proximal side of engagement plug 38 with respect to proximal seal 66, but because all of these surfaces are insulated, there is no or at least very minimal risk of an electrical short. The handles are preferably made of stainless steel or titanium. The tip assembly includes engagement plug 38 that is preferably made of cooper or plastic. Oversheath sleeve and spacer sleeve are preferably made of stainless steel or titanium. Proximal and distal seals are preferably made of silicone.

Figure 6:
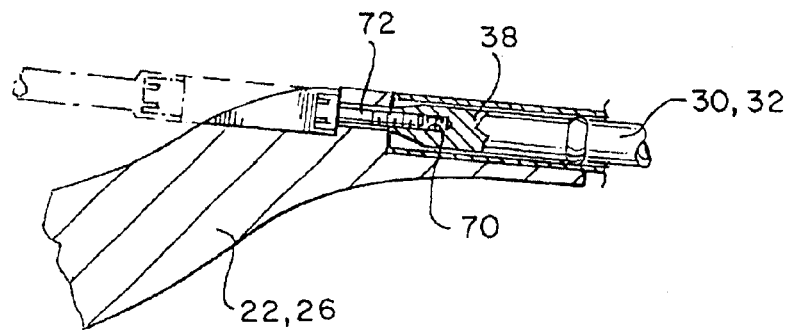
FIG. 6 is a partial cross-sectional view showing the tip assembly being selectively engaged with the insert tube by a threaded connection.

Referring now to FIG. 6, another manner in which the tip assembly can be selectively-engaged with the insert tubes is illustrated. The tip assembly 30, 32 is selectively engageable with the insert tube 22, 26 by a threaded connection. More specifically, the engagement plug 38 of the tip assembly includes a threaded bore 70 that mates with a threaded fastener 72. If desired, the head of the fastener 72 may be specially shaped to be opened by a specially-mating tool, not just a Phillips-head or flat-head screwdriver.

Referring now to FIG. 7, the threaded connection could also be achieved by using a knob 74 that is fixedly connected to threaded fastener 72. If desired, knob 74 can have a knurled outer surface that can be manually rotated to selectively engage the insert tube 22, 26 with the engagement plug 38 of the tip assembly 30, 32.

Referring now to FIG. 8, another embodiment for selectively engaging the tip assembly with the insert tube is illustrated. In this embodiment, the engagement plug includes a spring 76 that locks into a bore 77 in the insert tube 22, 26. The insert tube 22, 26 includes a plug 78. A distal end 79 of plug 78 includes a shaft that contacts the proximal end of engagement plug 38. To insert tip assembly 30, 32 into the insert tube 22, 26, the user will manually insert the tip assembly tube until spring 76 snaps into position within bore 77. To eject the tip assemblies 30, 32 from the insert tubes 22, 26, the user will need to simultaneously depress spring 77 and push on plug 78 until spring 76 clears bore 77 and is maintained in the down position by the internal cylindrical walls of insert tube 22, 26. Thereafter, the user may grasp the tip assembly 30, 32 and remove the tip assembly from the insert tube.

Referring now to FIGS. 9A–9C, another embodiment for selectively engaging the tip assembly with either the first or second insert tube is illustrated. In this embodiment, a first leaf spring 80 is fixedly attached to the engagement plug 38 of the tip assembly. A second leaf spring 82 is fixedly attached to a flag 84, which is disposed within a bore 86 in the proximal end 38 of the tip assembly. Flag 84 and second leaf spring 82 are together axially moveable to a predetermined extent with respect to the proximal end 38 of the tip assembly. A proximal end 88 of the first leaf spring 80 selectively engages in a bore 90 in the insert tube 22, 26. Similarly, second leaf spring 82 selectively engages in a second bore 92 in one of the insert tubes 22, 26. The insert tube further includes an axially moveable plug 94 that is terminated in a beveled distal axial end of cylinder 96. Upon depression of plug 94, the bevel 98 of cylinder 96 engages proximal end 88 of first leaf spring 80 to thereby remove first leaf spring 80 from bore 90 upon continued depression of plug 94 into the first or second insert tube 22, 26. Because leaf spring 80 is connected to the engagement plug 38, continued depression of plug 94 will cause engagement plug 38 to move distally with respect to the insert tube 22, 26 as illustrated in FIG. 9B. However, because cylinder 96 does not contact the second leaf spring 82, the flag 84 and second leaf spring 82 remain stationary with respect to the first or second insert tube 22, 26. The user may now remove the entire tip assembly from the insert tube 22, 26. Because the axial movement of flag 84 and second leaf spring 82 is limited, the second leaf spring 82 will be removed from bore 92 permitting the entire tip assembly to be removed from the insert tube 22, 26. However, upon removal, a portion of the flag will remain visible, protruding out from the proximal end of the tip assembly, thereby providing evidence to the operator that the tip assembly has been used.

Referring now to FIGS. 10 through 12, another embodiment showing the tip assembly being selectively engageable with the insert tube is illustrated. In this embodiment the tip assembly is selectively engageable with the insert tubes by a bayonette connection. The bayonette connection includes an elongated slot 102 in the tip assembly 30, 32 that mates with an elongated projection 104 projecting from one of the insert tubes 22, 26. To selectively disengage the tip assembly from the insert tube these elements are rotated approximately ninety degrees with respect to each other from the position illustrated in FIG. 10A, so that projection 104 aligns with slot 102. Thereafter, the tip assembly can be removed or disengaged from the insert tube. To engage the tip assembly with respect to the insert tube, the tip assembly is rotated into the position illustrated in FIG. 10B such that a detante 106 projecting from the insert tube snaps into a recess or bore 108 in the tip assembly.

Referring now FIGS. 13A and 13B, the tip assembly is shown having a weakened section 110. In addition, a nitinal ribbon 112 extends the length of the tip assembly 30, 32 and is attached to the tip assembly at the proximal end and the distal end. It is known that under thermal load, such as would occur during a steam sterilization cycle, that nitinal will contract approximately 4–8%. In contrast, the tip assembly will not contract. Thus, when the tip assembly is subjected to steam sterilization, the thermal loading is sufficiently large enough to cause the nitinal ribbon 112 to contract, thereby bending the tip assembly as shown in FIG. 13B at the weakened section 110. Thus, an operator will be able to readily determine that the tip assembly has been sterilized in an attempt to reuse the tip assembly.

Referring now to FIGS. 14A and 14B, the tip assembly includes a flag 114, 116 disposed in a recess 118, 120 of the tip assembly 30, 32. The flags 114, 116 are preferably made of nitinal, which, as discussed above, contract during thermal load, such as, for example, steam sterilization. Thus, once the tip assembly is subjected to steam sterilization, the nitinal flags 114, 116 will bend away from the tip assembly as illustrate in FIG. 14B, thereby making it clear to the user that the tip assembly has been used.

Figure 15:
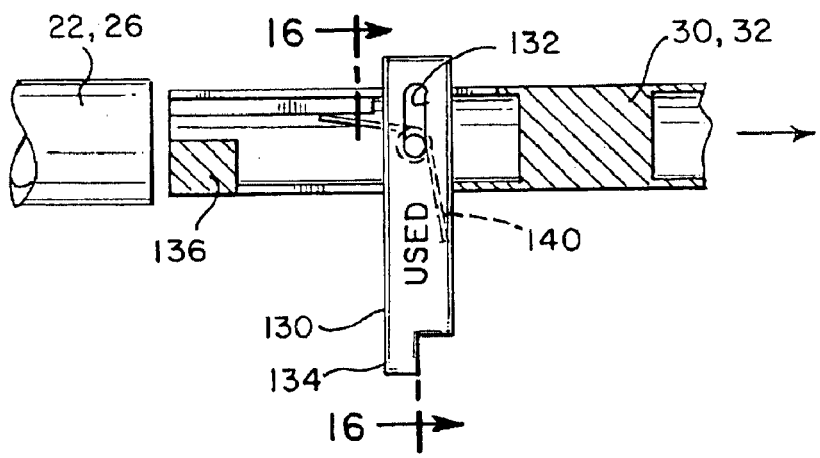
FIG. 15A is a partial side view of a tip assembly in accordance with another embodiment of the present invention.
FIG. 15B is a partial cross-sectional view of the tip assembly of FIG. 15A in the process of being disengaged with respect to the insert tube.
FIG. 15C is a partial cross-sectional view of the tip assembly of FIG. 15A, shown disengaged with respect to the insert tube.
Figure 16:
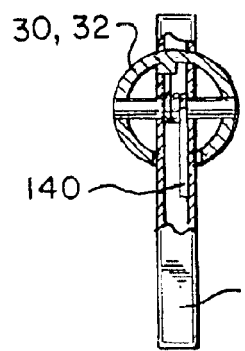
FIG. 16 is a cross-sectional view taken along lines 16—16 of FIG. 15C and looking in the direction of the arrows.

Referring now to FIGS. 15 and 16, another embodiment using a flag to point out to the operator that the tip assembly has been used is illustrated. More specifically, this embodiment uses a flag 130 that is axially moveable with respect to the engagement plug 38 of the tip assembly to a limited extent as determined by the length of the elongated slot 132 disposed within the proximal end 38 of the tip assembly. FIG. 15A illustrates the position of the tip assembly in the slot in the engaged position with respect to the insert tube. Flag 130 includes a notch portion 134 that rests upon a block 136 of the engagement plug 38. As the tip assembly is fully inserted into the insert tube 22, 26, the flag is released from resting upon block 136 by being moved by shaft 138, which is fixed to the insert tube 22, 26. Thus, flag 130 due to the bias applied by a spring 140, moves into the position illustrated in FIG. 15B. However, the inner surface of the insert tube 22, 26 prevents flag 130 from being fully deployed and releasing until the tip assembly 30, 32 is removed from the insert tube 22, 26. Once the tip assembly 30, 32 is removed, flag 130 is fully released by spring 140 to the position shown in FIG. 15C and FIG. 16, thereby making it quite evident to the operator that the tip has been used and should be disposed of properly.

Figure 17:
FIG. 17 is a partial perspective view of the tip assembly and insert tube in accordance with another embodiment of the present invention.
Figure 18:
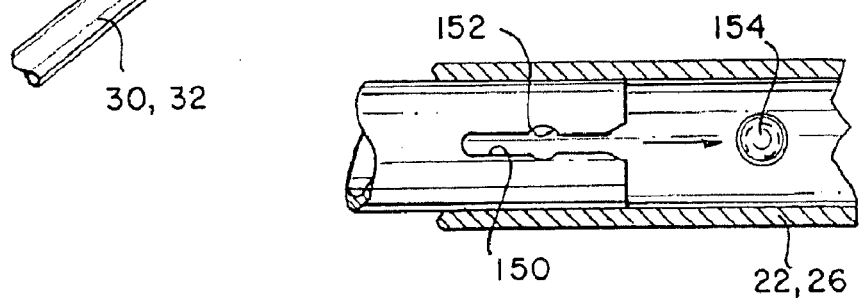
FIG. 18 is a partial top view of the tip assembly and insert tube of FIG. 17.

Referring now to FIGS. 17 and 18, another embodiment showing the tip assembly being selectively engageable with the insert tube is illustrated. In this embodiment, the proximal end of the tip assembly 30, 32, includes an open elongated slot 150 that has an enlarged portion 152. The insert tube 22, 26 includes a post 154 that has an enlarged sphere-shaped head. As the tip assembly 30, 32 is inserted into the insert tube, post 154 is received within slot 150 until it snaps into enlarged portion 152.

Figure 19:
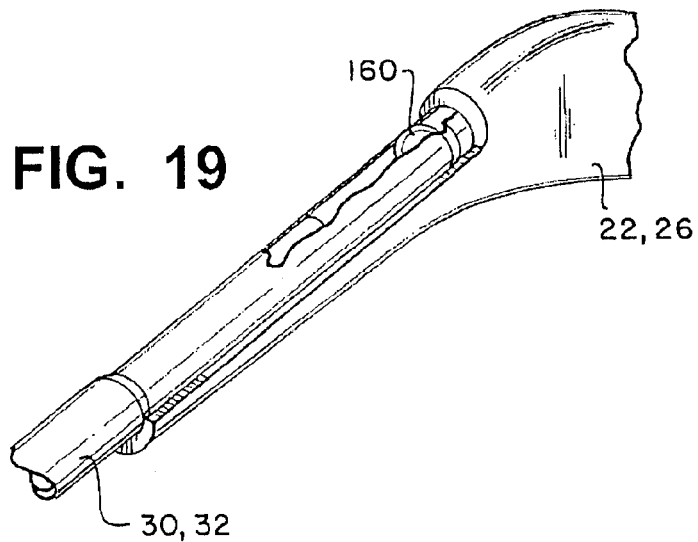
FIG. 19 is a partial perspective view of the tip assembly and insert tube in accordance with another embodiment of the present invention.
Figure 20:
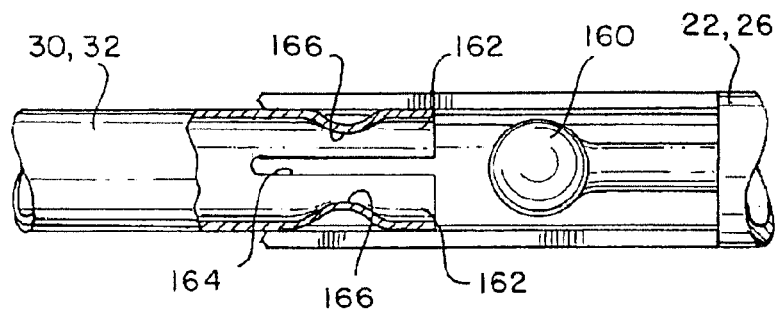
FIG. 20 is a top view of the tip assembly and insert tube of FIG. 19.
Figure 21:
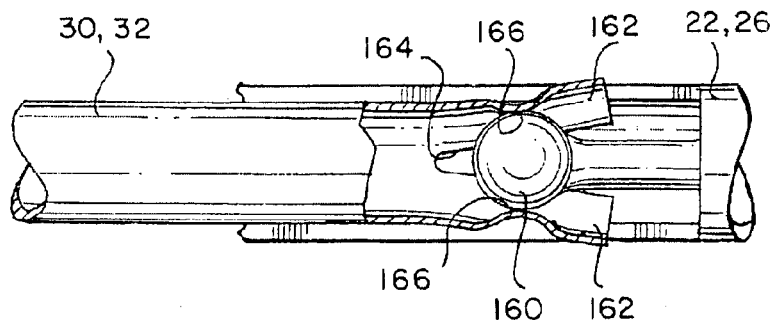
FIG. 21 is a partial top view of the tip assembly and insert tube of FIG. 19.

Referring now to FIGS. 19–21, another embodiment showing the tip assembly being selectively engageable with the insert tube is illustrated. In this embodiment, the insert tube 22, 26 includes a post 160 that has an enlarged sphere-shaped head projecting axially therefrom. The proximal end of the tip assembly 30, 32 has flexible fingers 162 formed by slots 164 cut into the proximal end of the tip assembly. The fingers preferably have an indented portion 166 that permit the post 160 to snap into the tip assembly 30, 32. FIGS. 17–21

Figure 22:
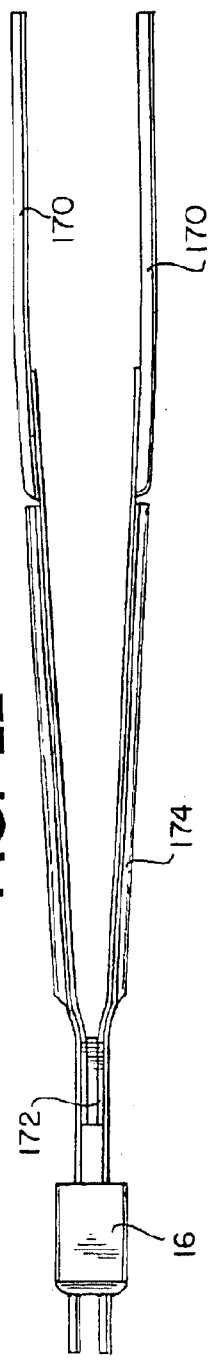
FIG. 22 is a top view of the tip assembly and insert tube in accordance with another embodiment of the present invention.
Figure 23:
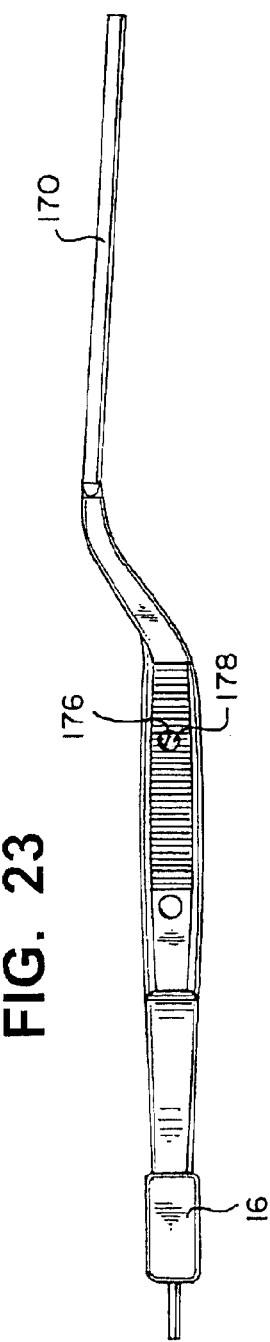
FIG. 23 is a side view of the tip assembly of the forceps shown in FIG. 22.
Figure 24:
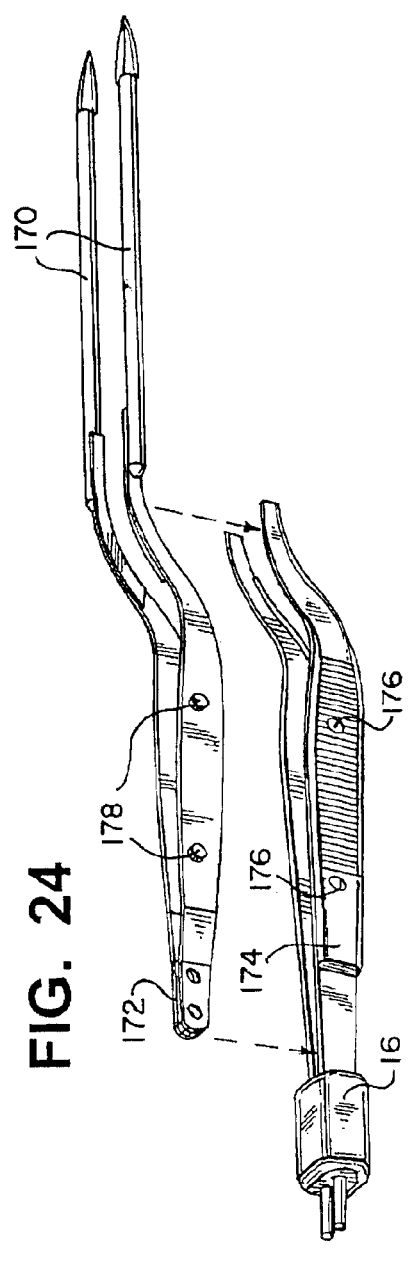
FIG. 24 is an exploded perspective view of the tip assembly and handle assembly in accordance with another embodiment of the present invention.

Referring now to FIGS. 22 and 23, another embodiment showing the tip assembly being selectively engageable with the insert tube is illustrated. In this embodiment, the tip assembly 170 is joined at its proximal end by an insulated spacer 172. The handle assembly 174 is connected to an electrical connector. The handles include a slot 176 that receive a retention projection 178 projecting outwardly from the tip assembly 170. To remove the tip assembly 170 from the handle assembly 174, the user may manually move the tip assembly together causing the projection 178 to be removed from slot 176. To insert the tip assembly 170 into the handle assembly 174, the user may manually move the tip assembly together and align the projection 178 with slot 176. Thereafter, the user may release the tip assembly causing the projection 178 to snap into slot 176. FIG. 24 shows a similar embodiment, but includes two projections 178 and two slots 176 on each handle.

Figure 25:
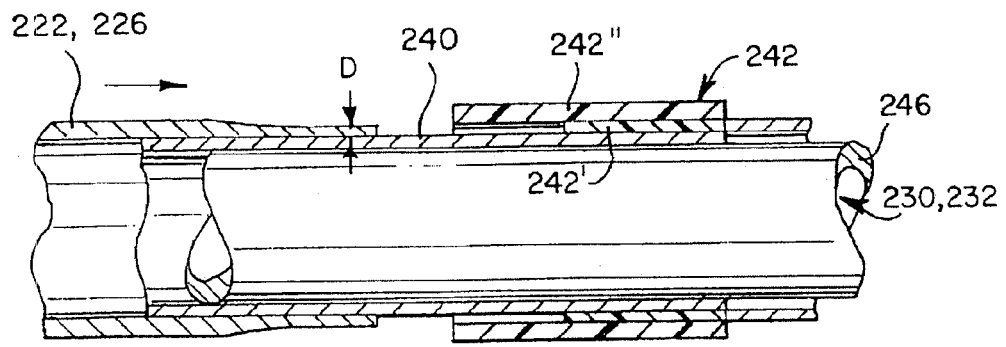
FIG. 25A is a partial cross-sectional view of the tip assembly and insert tube in accordance with another embodiment of the present invention.
FIG. 25B is a partial cross-sectional view of the tip assembly and insert tube of FIG. 25A shown in the engaged position.
FIG. 25C is a partial cross-sectional view of the tip assembly and insert tube in accordance with another embodiment of the present invention.
Figure 25:
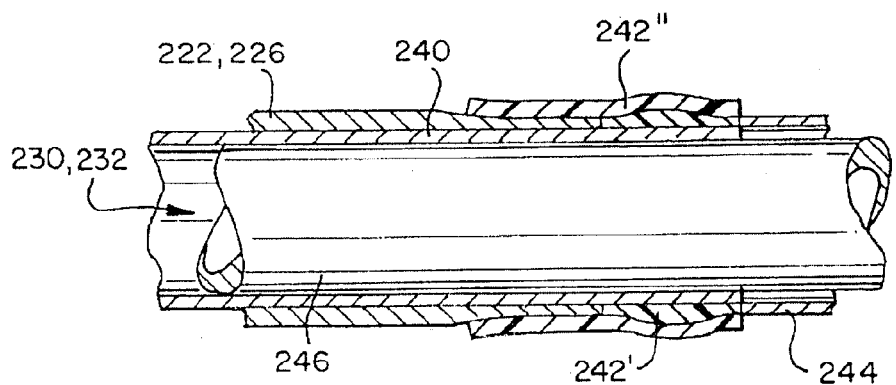
Figure 25:
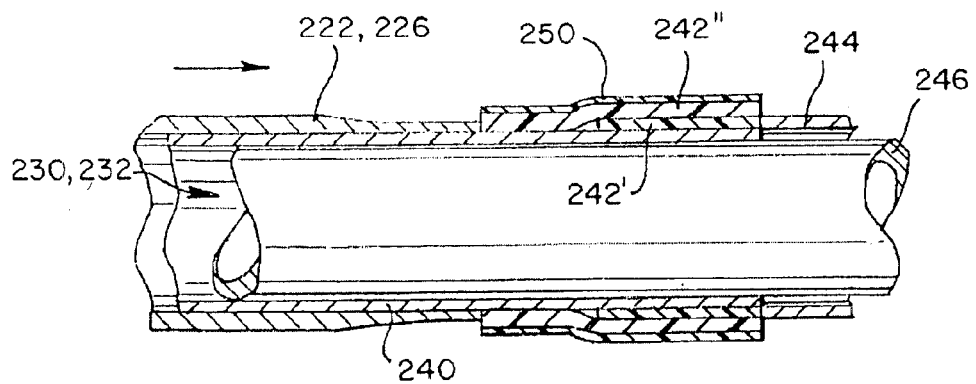

Referring now to FIGS. 25A–25C, another embodiment showing the tip assembly engaging with an insert tube is illustrated. As in all of the previous embodiments, for the sake of brevity in the disclosure, only those portions of this embodiment that vary with respect to the earlier described embodiments will be described in detail.

This electro-surgical bipolar forceps include a first member having a first insert tube 222 extending from a distal end thereof. A handle is disposed at a proximal end thereof. The first insert tube 222 has a distal end. A radial thickness D of the distal end of the first insert tube 222 is reduced, preferably by removing an electrically insulating layer on the outer surface thereof, to a predetermined dimension. Likewise, the forceps include a second member having a second insert tube 226 extending from a distal end thereof and a handle disposed at a proximal end thereof. The second insert tube 226 has a distal end. A radial thickness D of the distal end of the second insert tube 226 is preferably reduced to the same predetermined dimension.

A first tip assembly 230 and a second tip assembly 232 each have a proximal end and a distal end. The proximal end of the tip assemblies 230, 232 is selectively engageable with the first insert tube 222 and second insert tube 226, respectively. The tip assemblies including a first oversheath sleeve 240 disposed between the proximal end and the distal end. A first spacer sleeve 244 is disposed about the first oversheath sleeve 240. As pointed out above, spacer sleeve 244 may be of various lengths to vary the length of the tip assembly. Alternatively, no spacer sleeve may be used to shorten the tip assembly to its shortest dimension. In this situation, the distal seal 242 would be compressed between the tip and the insert tube 222, 226. A distal seal 242 is disposed about the oversheath sleeve and adjacent to a proximal end of the spacer sleeve 244. The distal seal 242 is comprised of an inner seal 242' and an outer seal 242". The outer seal 242" has a longitudinal length that is greater than a length of the inner seal 242'. The outer seal 242" has a portion spaced radially outwardly from the oversheath sleeve 240 by approximately the same predetermined dimension or slightly larger than the radial thickness of the distal end of the first and second insert tubes. The outer seal 242" is shown being made separate from inner seal 242' in the drawings, but the inner seal and outer seal could be made of one-piece construction. In the illustrated embodiment the inner seal is bonded, for example, by gluing, to the outer seal, and each of the seals are preferably made of silicone.

When the tip assembly is engaged with the insert tube, the inner seal portion 242' of the distal seal 242 is disposed in contact with and is compressed between the first spacer sleeve 244 and the first or second insert tube 222, 226, thereby applying a separating force between the first spacer sleeve 244 and the respective insert tube. The portion of the outer seal 242" that is spaced radially outwardly from the oversheath sleeve 240 is disposed radially about the distal end of the respective insert tube 222, 226 thereby providing additional electrical insulation between the insert tube and the spacer sleeve and/or the tip.

As illustrated in FIG. 25C, a heat shrinkable tube 250 is disposed about the outer seal portion 242" of the distal seal 242, such that when the tip assemblies are subject to heat exceeding a predetermined temperature, such as for a heat sterilization cycle, the heat shrinkable tube 250 will shrink thereby compressing the portion of the outer seal 242" that was originally spaced radially outwardly from the first oversheath sleeve 240 into contact with the first oversheath sleeve 240 as illustrated in FIG. 25C. Thus, should the tip assembly be subject to a steam sterilization cycle, one will be prevented from fully engaging the tip assembly with the insert tube because the outer seal 242" will effectively block the insertion of the tip assembly into the respective insert tube.

Having described the presently preferred exemplary embodiment of an electro-surgical bipolar forceps in accordance with the present invention, it is believed that other modifications, variations and changes will be suggested to those skilled in the art in view of the teachings set forth herein. It is, therefore, to be understood that all such modifications, variations, and changes are believed to fall within the scope of the present invention as defined by the appended claims. All publications and references cited herein are expressly incorporated herein by reference in their entirety.

What is claimed:

1. An electro-surgical bipolar forceps comprising:
    a first member having a first insert tube extending from a distal end thereof and a handle disposed at a proximal end thereof, the first insert tube having a distal end, a radial thickness of the distal end of the first insert tube being reduced to a predetermined dimension; and
    a first tip assembly having a proximal end and a distal end, the proximal end of the first tip assembly being selectively engageable with the first insert tube, the first tip assembly including a first oversheath sleeve disposed between the proximal end and the distal end, a first spacer sleeve disposed about the first oversheath sleeve, a first distal seal disposed about the first oversheath sleeve and adjacent to a proximal end of the first spacer sleeve, the first distal seal comprising of an inner seal and an outer seal, the outer seal having a longitudinal length that is greater than a length of the inner seal, the outer seal having a portion spaced radially outwardly from the first oversheath sleeve by approximately the same predetermined dimension as the radial thickness of the distal end of the first insert tube;
    wherein in the selectively engaged position, the inner seal portion of the first distal seal is disposed in contact with and is compressed between the first spacer sleeve and the first insert tube, thereby applying a separating force between the first spacer sleeve and the first insert tube, and the portion of the outer seal that is spaced radially outwardly from the first oversheath sleeve is disposed about the distal end of the first insert tube.

2. The electro-surgical bipolar forceps according to claim 1, wherein the first insert tube has an outer surface, a portion of the outer surface of the first insert tube is covered with an electrically insulating material.

3. The electro-surgical bipolar forceps according to claim 1, further comprising a heat shrinkable tube disposed about the outer seal portion of the first distal seal such that when the first tip assembly is subject to heat exceeding a predetermined temperature, the heat shrinkable tube compresses the portion of the outer seal that is originally spaced radially outwardly from the first oversheath sleeve into contact with the first oversheath sleeve.

4. An electro-surgical bipolar forceps comprising:
    a first member having a first insert tube extending from a distal end thereof and a handle disposed at a proximal end thereof, the first insert tube having a distal end, a radial thickness of the distal end of the first insert tube being reduced to a predetermined dimension;
    a second member having a second insert tube extending from a distal end thereof and a handle disposed at a proximal end thereof, the second insert tube having a distal end, a radial thickness of the distal end of the second insert tube being reduced to the predetermined dimension;
    a first tip assembly having a proximal end and a distal end, the proximal end of the first tip assembly being selectively engageable with the first insert tube, the first tip assembly including a first oversheath sleeve disposed between the proximal end and the distal end, a first spacer sleeve disposed about the first oversheath sleeve, a first distal seal disposed about the first oversheath sleeve and adjacent to a proximal end of the first spacer sleeve, the first distal seal comprising of an inner seal and an outer seal, the outer seal having a longitudinal length that is greater than a length of the inner seal, the outer seal having a portion spaced radially outwardly from the oversheath sleeve by approximately the same predetermined dimension as the radial thickness of the distal end of the first insert tube;
    a second tip assembly having a proximal end and a distal end, the proximal end of the second tip assembly being selectively engageable with the second insert tube, the second tip assembly including a second oversheath sleeve disposed between the proximal end and the distal end, a second spacer sleeve disposed about the second oversheath sleeve, a second distal seal disposed about the second oversheath sleeve and adjacent to a proximal end of the second spacer sleeve, the second distal seal comprising of an inner seal and an outer seal, the outer seal having a longitudinal length that is greater than a length of the inner seal, the outer seal having a portion spaced radially outwardly from the second oversheath sleeve by approximately the same predetermined dimension as the radial thickness of the distal end of the second insert tube;
    wherein in the selectively engaged position, the inner seal portion of the first distal seal is disposed in contact with and is compressed between the first spacer sleeve and the first insert tube, thereby applying a separating force between the first spacer sleeve and the first insert tube, and the portion of the outer seal that is spaced radially outwardly from the first oversheath sleeve is disposed about the distal end of the first insert tube, and the inner seal portion of the second distal seal is disposed in contact with and is compressed between the second spacer sleeve and the second insert tube, thereby applying a separating force between the second spacer sleeve and the second insert tube, and the portion of the outer seal that is spaced radially outwardly from the second oversheath sleeve is disposed about the distal end of the second insert tube.

5. The electro-surgical bipolar forceps according to claim 4, wherein the first insert tube and the second insert tube each has an outer surface, a portion of the outer surface of the first insert tube and the second insert tube is covered with an electrically insulating material.

6. The electro-surgical bipolar forceps according to claim 4, further comprising
    a first heat shrinkable tube disposed about the outer seal portion of the first distal seal such that when the first tip assembly is subject to heat exceeding a predetermined temperature, the first heat shrinkable tube compresses the portion of the outer seal that is originally spaced radially outwardly from the first oversheath sleeve into contact with the first oversheath sleeve, and a second heat shrinkable tube disposed about the outer seal portion of the second distal seal such that when the second tip assembly is subject to heat exceeding a predetermined temperature, the second heat shrinkable tube compresses the portion of the outer seal that is originally spaced radially outwardly from the second oversheath sleeve into contact with the second oversheath sleeve.

7. An electro-surgical bipolar forceps comprising:

a first member having a first insert tube extending from a distal end thereof and a handle disposed at a proximal end thereof, the first insert tube having a distal end, a radial thickness of the distal end of the first insert tube being reduced to a predetermined dimension; and a first tip assembly having a proximal end and a distal end, the proximal end of the first tip assembly being selectively engageable with the first insert tube, the first tip assembly including a first oversheath sleeve disposed between the proximal end and the distal end, a first tip disposed about the first oversheath sleeve, a first distal seal disposed about the first oversheath sleeve and adjacent to a proximal end of the first spacer sleeve, the first distal seal comprising of an inner seal and an outer seal, the outer seal having a longitudinal length that is greater than a length of the inner seal, the outer seal having a portion spaced radially outwardly from the first oversheath sleeve by approximately the same predetermined dimension as the radial thickness of the distal end of the first insert tube;

wherein in the selectively engaged position, the inner seal portion of the first distal seal is disposed in contact with and is compressed between the first tip and the first insert tube, thereby applying a separating force between the first tip and the first insert tube, and the portion of the outer seal that is spaced radially outwardly from the first oversheath sleeve is disposed about the distal end of the first insert tube.

8. The electro-surgical bipolar forceps according to claim 7, wherein the first insert tube has an outer surface, a portion of the outer surface of the first insert tube is covered with an electrically insulating material.

9. The electro-surgical bipolar forceps according to claim 7, further comprising a heat shrinkable tube disposed about the outer seal portion of the first distal seal such that when the first tip assembly is subject to heat exceeding a predetermined temperature, the heat shrinkable tube compresses the portion of the outer seal that is originally spaced radially outwardly from the first oversheath sleeve into contact with the first oversheath sleeve.

* * * * *